(12) United States Patent
Rongione et al.

(10) Patent No.: US 6,300,503 B1
(45) Date of Patent: Oct. 9, 2001

(54) HYDANTOIN INTERMEDIATES FOR THE SYNTHESIS OF OMAPATRILAT AND METHODS FOR PRODUCING AND USING THE SAME

(75) Inventors: Joseph C. Rongione, Highlands, NJ (US); Robert E. Brown, Houston, TX (US); Dwight E. Raff, Milford, NJ (US)

(73) Assignee: Dixie Chemical Company, Pasadena, TX (US)

( * ) Notice: Subject to any disclaimer, the term of this patent is extended or adjusted under 35 U.S.C. 154(b) by 0 days.

(21) Appl. No.: 09/589,571

(22) Filed: Jun. 7, 2000

Related U.S. Application Data
(60) Provisional application No. 60/172,335, filed on Dec. 17, 1999, and provisional application No. 60/172,440, filed on Dec. 17, 1999.

(51) Int. Cl.[7] .................. C07D 233/02; C07D 233/40
(52) U.S. Cl. ...................... 548/311.1; 548/319.1
(58) Field of Search ............... 548/311.1, 319.1

(56) References Cited

U.S. PATENT DOCUMENTS

| | | | |
|---|---|---|---|
| 3,424,783 | 1/1969 | Harper et al. | 260/465.5 |
| 3,862,203 | 1/1975 | Greco | 260/465.5 A |
| 4,039,527 | 8/1977 | Nagaoka et al. | 260/192 |
| 4,315,022 * | 2/1982 | Wotton et al. | 424/273 R |
| 4,543,215 | 9/1985 | Brunnmueller et al. | 260/465.5 R |
| 5,508,272 | 4/1996 | Robl | 514/80 |
| 5,663,363 * | 9/1997 | Elokdah et al. | 548/320.5 |
| 5,691,335 * | 11/1997 | Fukami et al. | 514/235.8 |

OTHER PUBLICATIONS

Robl et al., "Dual Metalloprotease Inhibitors: Mercaptoacetyl–Based Fused Heterocyclic Dipeptide Mimetics as Inhibitors of Angiotensin–Converting Enzyme and Neutral Endopeptidase," *J. Med. Chem.*, 1997, 40, 1570–1577, Princeton, New Jersey.

Robl Et Al., "Dual Metalloprotease Inhibitors. 6. Incorporation of Bicyclic and Substituted Monocyclic Azepinones as Dipeptide Surrogates in Angiotensin–Coverting Enzyme/Neutral Endopeptidase Inhibitors," *J. Med. Chem.*, 1996, 39, 494–502, Princeton, New Jersey.

Callahan, J. F., et al., "Synthesis of 6,6–Pentamethylene–2–aminosuberic Acid. A Key Intermediate in the Synthesis of Dicarba Analogues of Vasopressin Antagonists", Journal of Organic Chemistry, vol. 53, No. 7,1988, pp. 12527–30, XP–000984682

Rousset, A., et al. "Systèmes de strecker et Apparentés XI", vol. 36, 1980, pp. 2649–2661, XP002164112 p. 2649–2661.

Gaudry, R., "The Synthesis of D,L–α–Amino–ϵ–Hydroxycaproic Acid and a New Synthesis of D, L–Lysine" Canadian J. Res. Sect. B, vol. 26, 1948, pp. 387–392, XP000984801.

\* cited by examiner

*Primary Examiner*—Floyd G. Higel
*Assistant Examiner*—Golam M. M. Shameen
(74) *Attorney, Agent, or Firm*—Locke Liddell & Sapp LLP

(57) ABSTRACT

Omapatrilat (I) is a potent inhibitor of angiotensin-converting enzyme (ACE) and neutral endopeptidase (NEP) both in vitro and in vivo and is currently undergoing large scale clinical trials as an anti-hypertensive. Omapatrilat may be synthesized using the S-stereoisomer of compound (V). Compound (V) may be prepared from a novel hydantoin (III). The hydantoin may be prepared from a monoacetal (XI) or via a dinitrile (V).

38 Claims, No Drawings

HYDANTOIN INTERMEDIATES FOR THE SYNTHESIS OF OMAPATRILAT AND METHODS FOR PRODUCING AND USING THE SAME

This application claims priority from U.S. Provisional Application Ser. No. 60/172,335 filed Dec. 17, 1999 and U.S. Provisional Application Ser. No. 60/172,440 filed Dec. 17, 1999, both of which are incorporated herein by reference.

BACKGROUND OF THE INVENTION

Omapatrilat (I) is a potent inhibitor of angiotensin-converting enzyme (ACE) and neutral endopeptidase (NEP) both in vitro and in vivo:

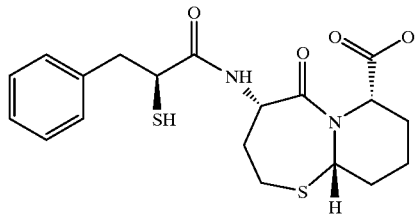

(I)

Omapatrilat was developed at the Bristol-Myers Squibb Pharmaceutical Research Institute as the first of a new class of compounds capable of simultaneously inhibiting ACE and NEP and is currently undergoing large scale clinical trials as an anti-hypertensive. See Omapatrilat. *Drugs R D* 1999 Apr;1(4):350–1.

Currently, omapatrilat is synthesized using (S)-hydroxy amino acid (II) as one of the key starting materials:

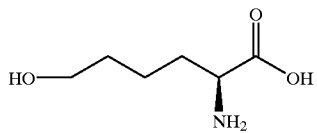

(II)

The hydroxyl group of compound (II) must be converted to an aldehyde as a prerequisite step in the syntheis of compound (I), omapatrilat. This oxidation to an aldehyde currently requires several steps and/or noxious reagents. See Robl, J. A., et al. *J. Med. Chem.* 1997, 40, 1570–1577; Robl, J. A. et al. *J. Med. Chem.* 1996, 39 494–502.

It is therefore desirable to find alternatives to compound (II) that reduce the number of requisite synthetic steps and eliminate the use of noxious reagents.

SUMMARY OF THE INVENTION

The invention is directed to novel compounds of the formula:

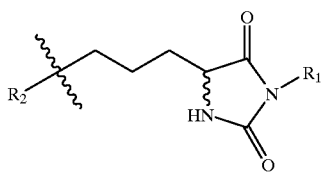

(III)

wherein $R_1$ is —H, a $C_1$–$C_5$ alkyl group or a benzyl group and $R_2$ is represented by one of the two following formulae:

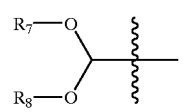

(VII)

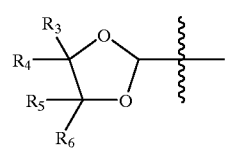

(VIII)

wherein $R_3$, $R_4$, $R_5$, and $R_6$ are independently selected from the group consisting of —H or a $C_1$–$C_5$ alkyl group and $R_7$ and $R_8$ are independently selected from the group consisting of a $C_1$–$C_5$ alkyl group.

The invention further relates to a method of producing and using the hydantoins of formula (III). Such compounds may be produced directly from a monoacetal (XI)

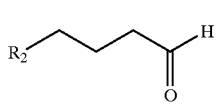

(XI)

or via a dinitrile intermediate of formula (IV):

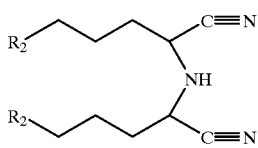

(IV)

Hydantoin (III) is an intermediate in the manufacture of racemic mixture (V):

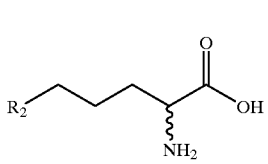

(V)

The S-stereoisomer, isolated from the racemic mixture, may be used, in place of compound (II), to produce omapatrilat. The overall reaction sequence for production of racemic mixture (V) is:

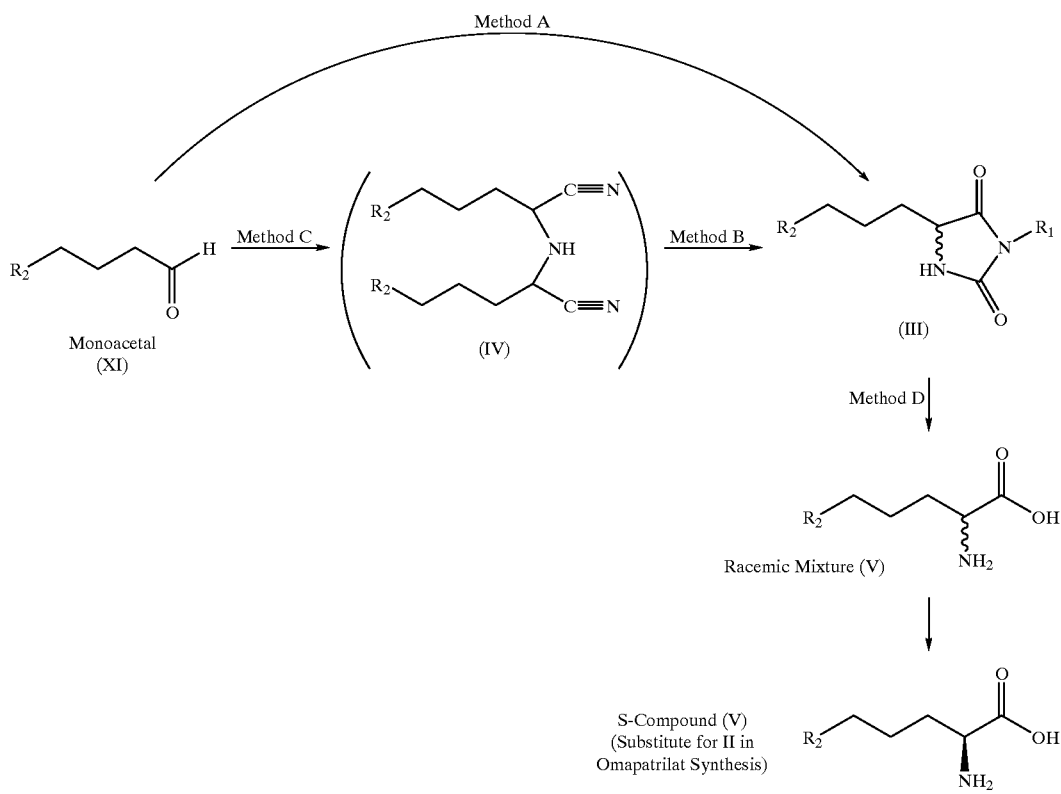

As used herein, "Method A" refers to the production of the novel hydantoin (III) of the invention directly from the monoacetal (XI). "Method B" refers to the production of the hydantoin via the dicyano intermediate and "Method C" refers to the production of the dicyano intermediate from the monoacetal (XI).

In another aspect of the invention, the novel hydantoin is employed to produce racemic mixture (V). The S-isomer, isolated from the racemic mixture, is used to produce omapatrilat. Production of the racemic from the novel hydantoin of the invention is referenced as "Method D."

The use of compound (V) with its protected aldehyde avoids the need to oxidize the alcohol on compound (II) and thus reduces the number of steps necessary for the synthesis of omapatrilat and further avoid the use of noxious chemicals. See Robl, J. A., et al. *J. Med. Chem.* 1997, 40, 1570–1577; Robl, J. A. et al. *J. Med. Chem.* 1996, 39, 494–502.

DETAILED DESCRIPTION OF PREFERRED EMBODIMENTS

The invention relates to novel hydantoin compounds of the formula (III):

(III)

and to processes of preparing the same. The invention further relates to a process of preparing a racemic mixture of formula (IV) from the hydantoin. The S-stereoisomer of the racemic mixture can be isolated and employed, as a substitute for formula (II), in the production of omapatrilat.

The hydantoin of the invention may be produced directly from the monoacetal of formula (XI) as well as via the dinitrile intermediate of formula (IV). The overall reaction sequence to generate the racemic mixture of formula (V) may be summarized as follows:

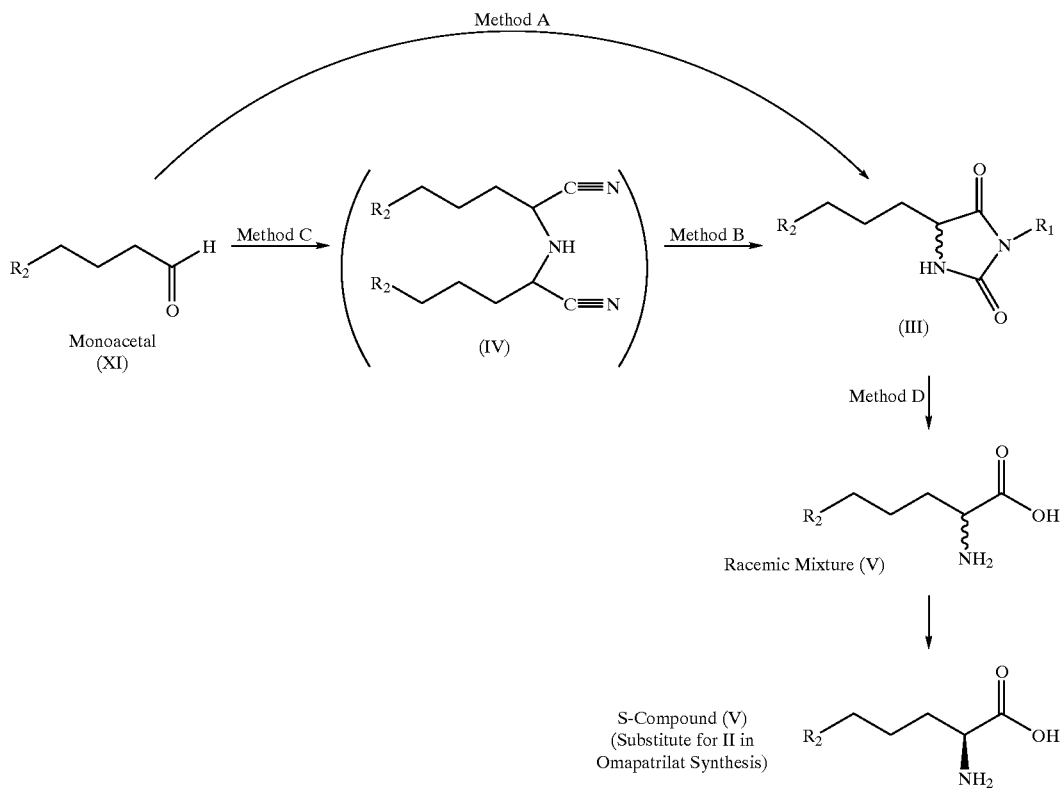

In the reaction sequence, $R_1$ is —H, a $C_1$–$C_5$ alkyl group or a benzyl group. In a preferred embodiment, $R_1$ is —H or a $C_1$–$C_3$ alkyl group. In the sequence above, $R_2$ is represented by either of the two following formulae,

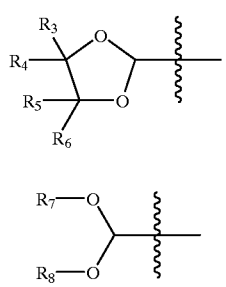

(VIII)

(VII)

wherein $R_3$, $R_4$, $R_5$, and $R_6$ are independently selected from the group consisting of —H or a $C_1$–$C_5$ alkyl group. (In a preferred embodiment $R_3$, $R_4$, $R_5$, and $R_6$ are independently selected from a group consisting of —H or a $C_1$–$C_3$ alkyl group. In a more preferred embodiment $R_3$, $R_4$, $R_5$, and $R_6$ are independently selected from the group consisting of a $C_1$–$C_3$ alkyl group; or $R_3$, $R_4$, $R_5$, and $R_6$ are all —H);

$R_7$ and $R_8$ are independently selected from a group consisting of a $C_1$–$C_5$ alkyl group. In a preferred embodiment $R_7$ and $R_8$ are independently selected from a group consisting of a $C_1$–$C_3$ alkyl group.

Where the dinitrile (IV) is employed, each of the $R_2$ groups may independently be selected from (VII) and (VIII). Compound (IV) can be used as a starting material for synthesis of hydantoin (III). Hydantoin (III) is used as an intermediate in the synthesis of compound (V):

The S stereoisomer of compound (V) may be obtained by subjecting the racemic mixture of formula (V) to amidation in water. A molar excess (generally 10 to 20 percent excess) of acetic anhydride is typically used to ensure complete acylation of all of the nitrogen groups on the compound of formula (V). The reaction is conducted at approximately 35° C. The amide linkage on the desired S-isomer may then be cleaved by enzymatic activity, thereby leaving the undesired R isomer in solution. The free amino acid is then collected and purified. The S stereoisomer of compound (V) may be purified in the same manner as the (S)-hydroxy amino acid compound (II) with a theoretical yield of 50%. (See Robl, J. A., et al. *J. Med. Chem.* 1997, 40, 1570–1577). The purified isomer may then be used to substitute for compound (II) as a synthetic starting material for generating omapatrilat.

An advantage in using compound (V) with its protected aldehyde is that it avoids the need to oxidize the alcohol on compound (II) and thus reduces the number of steps necessary for the synthesis of omapatrilat. It further avoids the use of noxious chemicals often employed in the oxidation of compound (II). See Robl, J. A., et al. *J. Med. Chem.* 1997, 40, 1570–1577; Robl, J. A., et al. *J. Med. Chem.* 1996, 39, 494–502.

An additional advantage in using compound (III) in the synthesis is the high efficiency evidenced when converting compound (III) to the S stereoisomer of compound (V). Hydantoins, such as compound (III), can be enzymatically racemized so that resolved R stereoisomer can be converted to and purified as the S stereoisomer, thereby increasing the possible yields of the desired S stereoisomer.

Compound (III) may be synthesized by either Method A or Method B. Method A is summarized below:

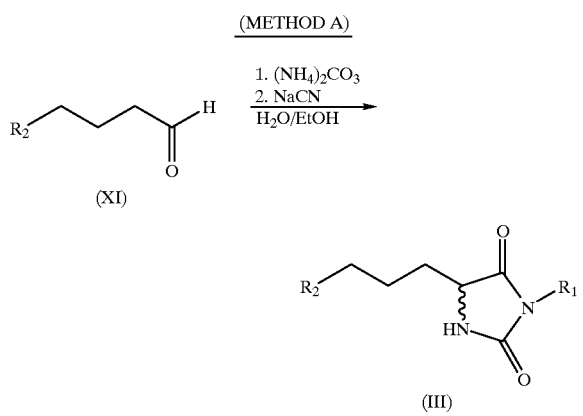

Any alkali cyanide, such as LiCN, as well as any organic cyanohydrin, such as a $C_1$–$C_6$ aliphatic cyanohydrin, may be used in place of NaCN in Method A. The reaction scheme for Method A presented above illustrates the use of a $H_2O$/EtOH blend as reaction medium, though a pure aqueous reaction medium may be used. The alcohol, which may be either methanol, ethanol, isopropyl alcohol, propyl alcohol, butyl alcohol or i-butyl alcohol, increases the solubility of the monoacetal of formula (I) in water. Typically, the weight ratio of water:$C_1$–$C_4$ alcohol in the reaction medium is 1:1 or more. The weight ratio of monoacetal:cyanide compound is typically between 2:1. The weight ratio of cyanide:ammonium carbonate is generally 1:13; and the weight ratio of reaction medium:monoacetal is typically 28:1.

In a preferred embodiment, the reaction mixture is heated above room temperature, (20° C.). In a more preferred embodiment, the reaction mixture is heated to about 50° C. to about 57° C. The reaction mixture is allowed to react for a time sufficient to effectuate the reaction, preferably more than 2 hrs and more preferably greater than 6 hrs and even more preferably greater than 12 hours. In a preferred embodiment, the reaction product is recovered by adjusting the system pH from about 6 to about 10, preferably about 7, at which time the reaction product forms a solid white powder. The reaction is conducted at ambient pressure. Method (A) may further generate a minor amount of compound (IV) as an intermediate chemical species.

The dicyano compound of formula (IV) is principally produced when the source of ammonium ion, i.e., ammonium carbonate in Method A, is replaced with another inorganic or an organic ammonium salt. The synthesis denoted as Method C may be schematically represented as:

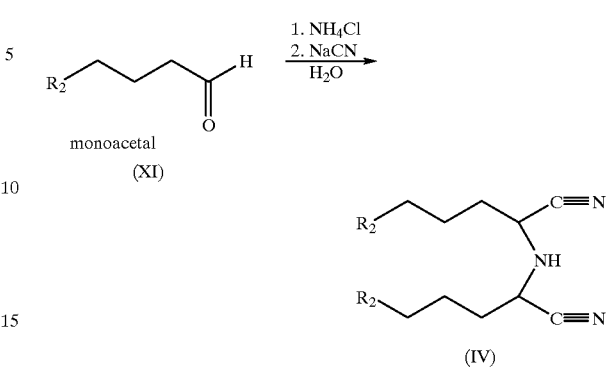

Suitable for use as the ammonium compound for Method C is ammonium chloride or any other inorganic ammonium compound, such as ammonium sulfate, or an organic containing ammonium compound. The cyano compound used in Method A may likewise be used in Method C. The weight ratio of ammonium compound:cyanide containing compound for Method C is generally about 1:1. In addition, the aqueous media in Method C may be substituted with a $C_1$–$C_4$ alkanol as discussed above for Method A. The weight ratio of reaction medium to monoacetal is about 4:1 and the weight ratio of cyanide containing compound:reaction medium is about 1:12.5.

In a preferred embodiment the reaction mixture for Method C is heated above room temperature (20° C.), preferably from 50° C. to about 52° C. at ambient temperature. The reaction mixture is allowed to react for an adequate amount of time to produce the compound of formula (IV), preferably more than 10 minutes, more preferably greater than 1 hour, and most preferably 2 hours or more. The pH of the reaction mixture is typically maintained between about 6 to about 10. In a preferred embodiment, the product is recovered from the organic phase by crystallization from acetone/water, more preferably followed by washing with toluene.

The dicyano compound of formula (IV) may then be converted to compound (III) as shown in Method (B):

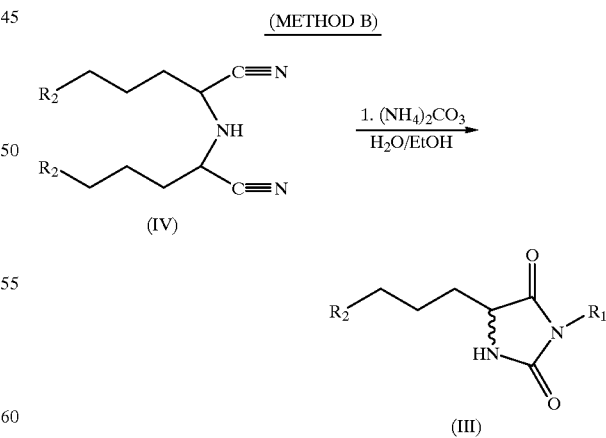

Thus, the use of a non-carbonate inorganic ammonium salt, such as ammonium chloride, or an organo ammonium containing compound (versus ammonium carbonate), causes the formation of the dicyano compound (III). Conversion of the dicyano compound (IV) to the hydantoin (Ill) requires the additional step of reacting the intermediate compound (IV) with carbon dioxide or a carbon dioxide generating compound such as ammonium carbonate. In a preferred embodiment, the addition of an alkali or ammonium hydroxide is also used in order to assist in the formation of the carbon dioxide. The weight ratio of carbon dioxide or carbon dioxide generating compound:hydroxide is generally between 1:1.75 and the weight ratio of carbon dioxide or carbon dioxide generating compound:reaction medium is generally 1:7.5.

In place of the $H_2O$/EtOH mixture, the reaction media can be purely water or any a mixture of any of the $C_1$–$C_4$ alcohols referenced above. The reaction mixture in Method B is allowed to proceed generally at room temperature and at ambient or above atmospheric pressure (up to about 60 psig) for 10 minutes or more, more preferably for 2 hours or more and even more preferably for at least 6 hours at a pH of between from about 6 to about 10. In a preferred embodiment, the solution is brought to a pH of 7.5.

Compound (V) is produced from the hydantoin as summarized in Method D:

(METHOD D)

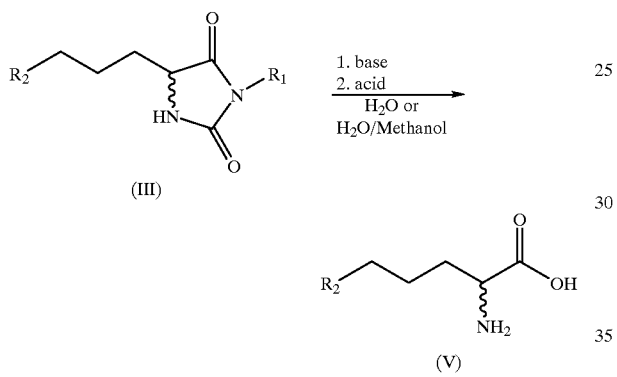

The base in the reaction mixture of Method D is an alkali hydroxide, preferably either sodium hydroxide or lithium hydroxide, and the acid is preferably acetic acid, dilute hydrochloric acid or sulfuric acid, most preferably acetic acid. The weight ratio of hydantoin to alkali hydroxide to reaction media is about 1:1:6. In a preferred embodiment the reaction mixture (D) is heated above room temperature (20° C.) and in a more preferred embodiment is heated to 100° C. or higher, and in an even more preferred embodiment is heated to 150° C. The reaction mixture is allowed to react for an adequate amount of time to produce the desired racemic mixture. This adequate reaction time is preferably more than 10 minutes and more preferably greater than 1 hour and even more preferably greater than 2 hours. During the reaction, the pH increases to about 12 or higher. The reaction mixture (D) is brought to pH 7 with the acid. The weight ratio of base:acid in the reaction is generally about 1:1.4.

The following examples will illustrate the practice of the present invention in its preferred embodiments. Other embodiments within the scope of the claims herein will be apparent to one skilled in the art from consideration of the specification and practice of the invention as disclosed herein. It is intended that the specification, together with the examples, be considered exemplary only, with the scope and spirit of the invention being indicated by the claims which follow.

EXAMPLE 1

Synthesis of Representative Species of Compound (IV) wherein $R_2$ is Formula (VIII)

Water (30 g), glutaric dialdehyde monoethylene glycol acetal (monoacetal, 15.1 g) and ammonium chloride (5.58 g) were added together in a 100 mL round bottom flask (mixing by magnetic stirrer). Next sodium cyanide (4.80 g in 20.9 g water) was added. A 16° C. temperature rise was noted. The reaction mixture was heated to 50–52° C. and held at this temperature for 2 hours. The lower organic phase was separated from the upper aqueous phase. The aqueous phase was twice washed with methylene chloride. After solvent removal, the oil was crystallized from acetone/water. After washing with toluene, the white solid was dried.

$^1$H NMR data (300 MHz, $(CD_3)_2SO$): δ1.5–1.9 (m, 12H), 3.76 (m, 1H), 3.8–4.0 (m, 10H 4.8 (m, 2H). $^{13}$C NMR data (75 MHz, $(CD_3)_2SO$): δ19.6, 32.5, 33.2, 48.1 64.2, 103.4, 120.0. Mass Spectroscopy data (+CI) m/z (relative intensity): 297 ($M^+$ –HCN, 21), 270 ($M^+$ –2 HCN, 27), 235 ($M^+$ —HCN,$CH_2CH_2O$, $H_2O$, 25), 208 ($M^+$ –2 HCN, $CH_2CH_2O$, $H_2O$, 100). Anal. Calcd for $C_{16}H_{25}N_3O_4$: C, 59.43; H, 7.79; N, 12.99. Found: C, 59.48; H, 7.92; N, 12.87.

End product $C_{16}H_{25}N_3O_4$, Compound (IX), is represented by the formula:

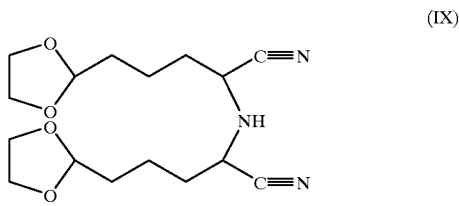

(IX)

EXAMPLE 2

Synthesis of Representative Species of Compound (IV) wherein $R_2$ is Formula (VII)

The procedure set forth in Example 1 is repeated. In place of glutaric dialdehyde monoethylene glycol acetal, about 15 g of glutaric dialdehyde dimethanol acetal is used. All other reaction conditions may remain the same.

EXAMPLE 3

Synthesis Representative Species of Compound (III) wherein $R_2$ is Formula (VIII)

Water (190 g) was added to a 2 liter round bottom flask (mechanically stirred). Next, ammonium carbonate (174.9 g) was added to the water. More water (195 g) and ethanol (385 g) were added to the flask, followed by sodium cyanide (13.3 g). Glutaric dialdehyde monoethylene glycol acetal (monoacetal, 30.0 g) was added in one portion. A 7° C. temperature rise was noted. The reaction mixture was heated to 50–57° C. and held at this temperature for 12.3 hours. The reaction volume was reduced (490.8 g taken as overhead). System pH was brought to 7 with 25% $H_2SO_4$ at which time a solid white powder formed in the flask. The solid was recrystallized from water and dried.

End product, compound (X), is represented by the formula:

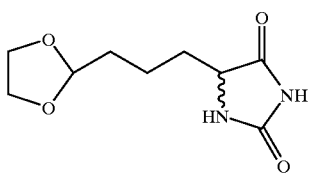

(X)

EXAMPLE 4

Synthesis Representative Species of Compound (III) wherein $R_2$ is formula (VII)

The procedure set forth in Example 3 is repeated. In place of glutaric dialdehyde monoethylene glycol acetal, about 30 g of glutaric dialdehyde monomethanol acetal is used. All other reaction conditions may remain the same.

EXAMPLE 5

Second Synthesis Scheme for Representative Species of Compound (III)

Water (30 g), glutaric dialdehyde monoethylene glycol acetal (monoacetal, 15.1 g) and ammonium chloride (5.58 g) were added together in a 100 mL round bottom flask (on a magnetic stirrer). Next, sodium cyanide (4.80 g in 20.9 g water) was added over 10 minutes. The reaction was heated to 50–52° C. and held at this temperature for 2 hours. Both phases were transferred to a pressure vessel. The system was heated to 100° C. and carbon dioxide was fed to the reactor. Maximum system pressure was 60 psig. After 6 hours, the solution was cooled and brought to pH 7.5 with acetic acid. The hydantoin was recovered as a white solid.

EXAMPLE 6

Synthesis of Racemic Mixture of Formula (V)

Ammonium chloride (90.8 g, 1.70 moles) in water (1000 g) was cooled to 0–5 C. Next, monoacetal (246 g. 1.17% dialdehyde, 3.56% bisacetal, 1.63 moles) was added to the ammonium chloride solution. While maintaining the system temperature between 0–10 C. sodium cyanide (79.3 g, 1.62 moles; in 313.4 g water and 3.9 g 50% NaOH aq. Soln., CAUTION: toxic, exotherm) was added below the surface of the monoacetal solution. Upon completion of the addition the solution was heated to 50° C. for six hours. The solution was cooled to 30° C. Ammonium hydroxide (211 g, 2.22 equivalents; 28–30% in water) was charged and the solution was reheated to 100° C. Gaseous carbon dioxide (133.2 g, slight exotherm) was fed to the reactor at such a rate as to maintain system pressure near 60–65 psig and the reaction temperature at 100° C. The system was held at 100° C. for four hours. Excess carbon dioxide was vented from the system. A portion of the water was boiled overhead to facilitate the removal of ammonia and to make room for the next step. Lithium hydroxide (226.4 g, 3.33 equivalents; 10% in water) was added after the water strip. The system was brought to 150° C. for four hours. The reaction system was then cooled, filtered (235.2 g wet cake) and neutralized with acetic acid (310 g) to a pH of 7.2–7.4. After a water strip (1878.3 g overhead) methanol (2400 g) was added to precipitate the racemic amino acid. The white solid was washed with cold methanol after recovery. A racemic mixture of formula (V) wherein $R_2$ is (VIII) was obtained.

What is claimed is:

1. A compound of the formula:

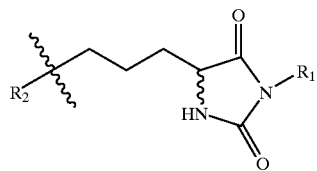

wherein $R_1$ is —H, a $C_1$–$C_5$ alkyl group or benzyl, and $R_2$ is represented by the formula:

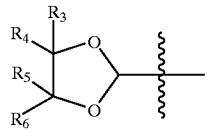 or 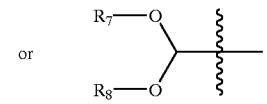

wherein $R_3$, $R_4$, $R_5$, and $R_6$ are independently selected from the group consisting of —H or a $C_1$–$C_5$ alkyl group and $R_7$ and $R_8$ are independently selected from the group consisting of a $C_1$–$C_5$ alkyl group.

2. The compound of claim 1, wherein $R_2$ is of the formula:

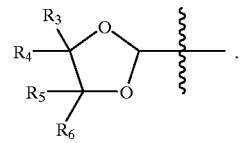

3. The compound of claim 2, wherein $R_3$, $R_4$, $R_5$, and $R_6$ are independently selected from the group consisting of —H or a $C_1$–$C_3$ alkyl group.

4. The compound of claim 3, wherein $R_3$, $R_4$, $R_5$, and $R_6$ are all hydrogen.

5. The compound of claim 2, wherein $R_1$ is hydrogen.

6. The compound of claim 1, wherein $R_1$ is hydrogen.

7. The compound of claim 1, wherein $R_1$ is a $C_1$–$C_5$ alkyl group.

8. The compound of claim 5, wherein $R_3$, $R_4$, $R_5$, and $R_6$ are all hydrogen.

9. The compound of claim 1, wherein $R_2$ is

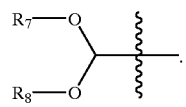

10. The compound of claim 9, wherein $R_7$ and $R_8$ are independently selected from the group consisting of a $C_1$–$C_3$ alkyl group.

11. The compound of claim 9, wherein $R_1$ is —H.

12. The compound of claim 9, wherein $R_1$ is a $C_1$–$C_5$ alkyl group.

13. The compound of claim 9, wherein $R_1$ is benzyl.

14. A process of preparing a compound of the formula:

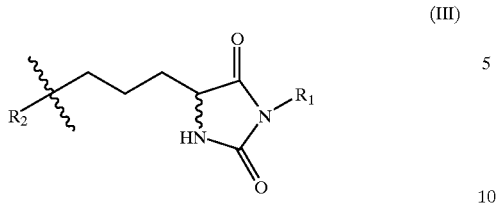

(III)

wherein $R_1$ is —H, a $C_1$–$C_5$ alkyl group, or benzyl and $R_2$ is represented by the formula:

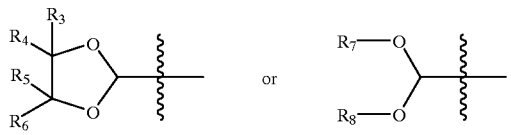

or wherein $R_3$, $R_4$, $R_5$, and $R_6$ are independently selected from the group consisting of —H or a $C_1$–$C_5$ alkyl group and $R_7$ and $R_8$ are independently selected from the group consisting of a $C_1$–$C_5$ alkyl group, said process comprising mixing monoacetal having the formula:

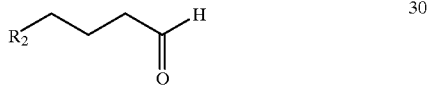

with ammonium carbonate and either an alkali cyanide or a cyanohydrin for a time and at a temperature sufficient to render a compound of formula (III).

15. The process of claim 14, wherein the mixture is maintained at a temperature greater than 20° C.

16. The process of claim 14, wherein the alkali cyanide is sodium or lithium cyanide.

17. The process of claim 15, wherein the mixture is maintained at a temperature of between about 50° C. to about 57° C.

18. The process of claim 14, wherein the monoacetal and ammonium carbonate are admixed for at least 2 hours.

19. The process of claim 14, wherein $R_2$ is

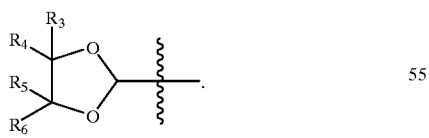

20. The process of claim 14, wherein $R_2$ is:

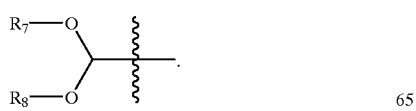

21. A compound of the formula:

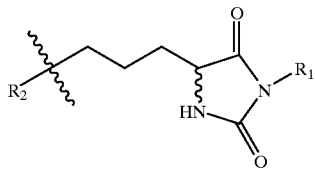

wherein $R_1$ is —H, a $C_1$–$C_5$ alkyl group, or benzyl and $R_2$ is represented by the formula:

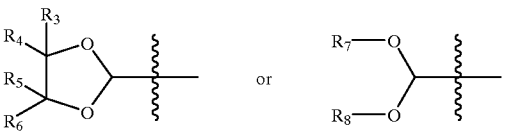

or and further wherein $R_3$, $R_4$, $R_5$, and $R_6$ are independently selected from the group consisting of —H or a $C_1$–$C_5$ alkyl group and $R_7$ and $R_8$ are independently selected from the group consisting of a $C_1$–$C_5$ alkyl group, produced by the process of claim 14.

22. A process of preparing a hydantoin of the formula:

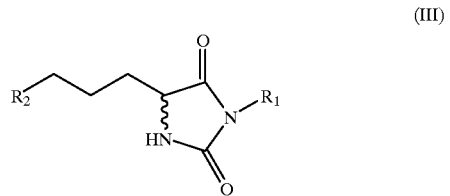

(III)

wherein $R_1$ is —H, a $C_1$–$C_5$ alkyl group, or benzyl and $R_2$ is represented by the formula:

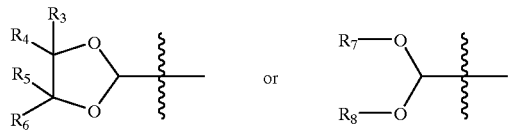

or wherein $R_3$, $R_4$, $R_5$, and $R_6$ are independently selected from the group consisting of —H or a $C_1$–$C_5$ alkyl group and $R_7$ and $R_8$ are independently selected from the group consisting of a $C_1$–$C_5$ alkyl group, said process comprising mixing a dinitrile having the formula:

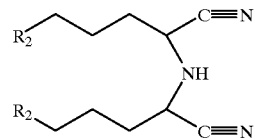

with carbon dioxide or a carbon dioxide generating compound in an aqueous medium for a time and at a temperature sufficient to generate the compound of formula (III).

23. The process of claim 22, wherein the carbon dioxide generating compound is ammonium carbonate.

24. The process of claim 22, wherein the reaction proceeds at a pressure from about ambient to about 60 psig.

25. The process of claim 22, wherein the dinitrile and carbon dioxide or carbon dioxide generating compound are admixed for at least 10 minutes.

26. The process of claim 25, wherein the dinitrile and carbon dioxide or carbon dioxide generating compound are admixed for at least 2 hours.

27. The process of claim 26, wherein the dinitrile and carbon dioxide or carbon dioxide generating compound are admixed for at least 6 hours.

28. A hydantoin of the formula (III):

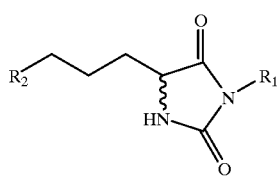

(III)

wherein $R_1$ is —H, a $C_1$–$C_5$ alkyl group, or benzyl and $R_2$ is represented by the formula:

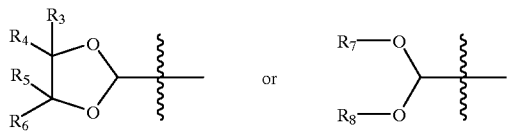

or wherein $R_3$, $R_4$, $R_5$, and $R_6$ are independently selected from the group consisting of —H or a $C_1$–$C_5$ alkyl group and $R_7$ and $R_8$ are independently selected from the group consisting of a $C_1$–$C_5$ alkyl group produced by the process of claim 22.

29. A process of preparing a compound of the formula:

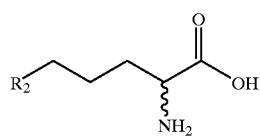

(V)

wherein $R_2$ is either

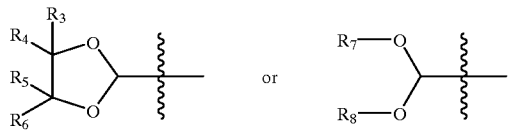

or wherein $R_3$, $R_4$, $R_5$, and $R_6$ are independently selected from the group consisting of —H or a $C_1$–$C_5$ alkyl group and $R_7$ and $R_8$ are independently selected from the group consisting of a $C_1$–$C_5$ alkyl group, said process comprising mixing a hydantoin having the formula:

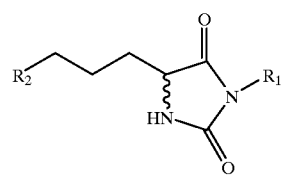

wherein $R_1$ is —H, a $C_1$–$C_5$ alkyl group or benzyl under alkaline conditions for a time and at a temperature sufficient to generate the compound of formula (V).

30. The process of claim 29, wherein the mixture is heated at a temperature between from about 100° to about 150° C.

31. The process of claim 29, wherein the alkaline is the combination of an alkali hydroxide and an acid.

32. The process of claim 31, wherein the acid is acetic acid.

33. The process of claim 29, wherein the hydantoin is prepared by mixing monoacetal having the formula:

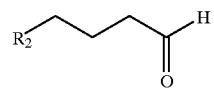

with ammonium carbonate and an alkali cyanide or a cyanohydrin for a time and at a temperature sufficient to render the hydantoin.

34. The process of claim 33, wherein the hydantoin and acetal are mixed at a temperature of from about 50° C. to about 57° C.

35. The process of claim 33, wherein $R_2$ is

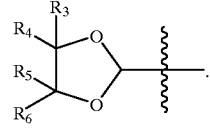

36. The process of claim 29, wherein the hydantoin is prepared by mixing a dinitrile having the formula:

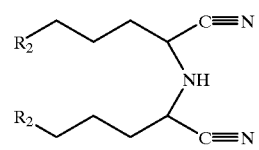

with carbon dioxide or a carbon dioxide generating compound in an aqueous medium for a time and at a temperature sufficient to generate the hydantoin.

37. The process of claim 36, wherein the mixture is heated at about at a temperature from about 100° to about 150° C. at a pressure from about ambient to about 60 psig.

38. The process of claim 36, wherein the dinitrile is prepared by mixing monacetal having the formula:

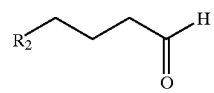

with a non-carbonate ammonium salt and an alkali cyanide for a time and at a temperature sufficient to generate the dinitrile.

* * * * *